United States Patent [19]
Portney

[11] Patent Number: 5,877,839
[45] Date of Patent: Mar. 2, 1999

[54] MULTIFOCAL OPHTHALMIC LENS

[76] Inventor: Valdemar Portney, 7 Alassio, Irvine, Calif. 92720

[21] Appl. No.: 811,985

[22] Filed: Mar. 5, 1997

Related U.S. Application Data

[62] Division of Ser. No. 592,164, Jan. 26, 1996, Pat. No. 5,657,108, which is a division of Ser. No. 122,822, Sep. 16, 1993, Pat. No. 5,521,656, which is a division of Ser. No. 935,586, Aug. 26, 1992, Pat. No. 5,270,744, which is a division of Ser. No. 465,477, Jan. 16, 1990, Pat. No. 5,166,712, which is a division of Ser. No. 366,319, Jun. 14, 1989, Pat. No. 4,898,461, which is a continuation of Ser. No. 56,050, Jun. 1, 1987, abandoned.

[51] Int. Cl.$^6$ .................................. G02C 7/04; A61F 2/16
[52] U.S. Cl. ................................ 351/161; 351/177; 623/6
[58] Field of Search .......................... 351/160 R, 160 H, 351/161, 162, 169, 177; 623/6

[56] References Cited

U.S. PATENT DOCUMENTS

| | | | |
|---|---|---|---|
| Re. 25,286 | 11/1962 | DeCarle | 351/161 |
| 1,483,509 | 2/1924 | Bugbee | 351/169 |
| 2,123,305 | 9/1938 | Feinbloom | 351/160 R |
| 2,274,142 | 2/1942 | Houchin | 351/168 |
| 2,405,989 | 8/1946 | Beach | 351/169 |
| 2,511,517 | 6/1950 | Spiegel | 69/77 |

(List continued on next page.)

FOREIGN PATENT DOCUMENTS

| | | |
|---|---|---|
| 159395 | 12/1914 | Canada . |
| 0064812 | 11/1982 | European Pat. Off. . |
| 0169599 | 1/1986 | European Pat. Off. . |
| 3246306 | 6/1984 | Germany . |
| 2702117 | 7/1987 | Germany . |
| 253097A5 | 1/1988 | Germany . |
| 58-143316 | 8/1983 | Japan . |
| 939016 | 10/1963 | United Kingdom . |
| 2058391 | 4/1981 | United Kingdom . |
| 2129155 | 5/1984 | United Kingdom . |
| 2146791 | 4/1985 | United Kingdom . |
| WO86/03961 | 7/1986 | WIPO .................................... 351/161 |
| WO87/00299 | 1/1987 | WIPO .................................... 351/161 |
| WO87/07496 | 12/1987 | WIPO . |

OTHER PUBLICATIONS

"The Shah Bifocal Intraocular Lens Implant", Shah & Shah Intraocular Lens Laboratories, Calcutta, India.
Contact Lens Practice, 1998, pp. 211, 212, 403, 404, 491 and 792.
Encyclopedia of Contact Lens Practice, Sep. 1, 1960, pp. 24–26.
Further Developments of Bifocal Contact Lenses, Aug. 1959, pp. 185–186.

*Primary Examiner*—Scott J. Sugarman
*Attorney, Agent, or Firm*—Frank J. Uxa

[57] ABSTRACT

An improved opthalmic lens is disclosed which has a plurality of alternating power zones with a continuously varying power within each zone, as well as in transition from one zone to another. In other words, a plurality of concentric zones (at least two) are provided in which the variation from far to near vision correction is continuous, i.e., from near correction focal power to far correction focal power, then back to near, and again back to far, or vice versa. This change is continuous (progressive), without any abrupt correction changes, or "edges".

Two versions of the invention are disclosed. In the first version continuous, alternating power variation is accomplished by a continuously changing curvature of the lens posterior surface, thereby altering the angle of impact of light rays on the eye.

In the second version continuous, alternating power variation is accomplished by creating non-homogeneous surface characteristics having refractive material indexes which continuously vary in the lens radial direction (out from the optical axis).

19 Claims, 7 Drawing Sheets

U.S. PATENT DOCUMENTS

| | | | |
|---|---|---|---|
| 3,004,470 | 10/1961 | Ruhle | 351/168 |
| 3,031,927 | 5/1962 | Wesley | 351/161 |
| 3,034,403 | 5/1962 | Neefe | 351/162 |
| 3,210,894 | 10/1965 | Bentley | 51/284 R |
| 3,227,507 | 1/1966 | Feinbloom | 351/160 R |
| 3,339,997 | 9/1967 | Wesley | 351/161 |
| 3,420,006 | 1/1969 | Barnett | 51/129 |
| 3,431,327 | 3/1969 | Tsuetaki | 351/161 |
| 3,482,906 | 12/1969 | Volk | 351/160 R |
| 3,542,461 | 11/1970 | Girard et al. | 351/160 R |
| 3,610,924 | 10/1971 | Sinai | 351/169 |
| 3,693,301 | 9/1972 | Lemaltre | 51/284 R |
| 3,794,414 | 2/1974 | Wesley | 351/161 |
| 3,932,148 | 1/1976 | Krewalk, Sr. | 51/284 R |
| 4,055,378 | 10/1977 | Feneberg et al. | 351/160 H |
| 4,062,629 | 12/1977 | Winthrop | 351/169 |
| 4,073,579 | 2/1978 | Deeg et al. | 351/169 |
| 4,162,122 | 7/1979 | Cohen | 351/161 |
| 4,195,919 | 4/1980 | Shelton | 351/160 R |
| 4,199,231 | 4/1980 | Evans | 351/161 |
| 4,210,391 | 7/1980 | Cohen | 351/161 |
| 4,240,719 | 12/1980 | Guilino et al. | 351/169 |
| 4,274,717 | 6/1981 | Davenport | 351/169 |
| 4,307,945 | 12/1981 | Kitchen et al. | 351/169 |
| 4,315,673 | 2/1982 | Guilino et al. | 351/169 |
| 4,338,005 | 7/1982 | Cohen | 351/161 |
| 4,340,283 | 7/1982 | Cohen | 351/161 |
| 4,377,329 | 3/1983 | Polar | 351/160 R |
| 4,402,579 | 9/1983 | Polar | 351/160 R |
| 4,418,991 | 12/1983 | Breger | 351/161 |
| 4,504,982 | 3/1985 | Burk | 623/6 |
| 4,573,775 | 3/1986 | Bayshore | 351/161 |
| 4,580,882 | 4/1986 | Nuchman et al. | 351/161 |
| 4,596,578 | 6/1986 | Kelman | 623/6 |
| 4,618,228 | 10/1986 | Baron et al. | 351/161 |
| 4,618,229 | 10/1986 | Jacobstein et al. | 351/161 |
| 4,635,049 | 1/1987 | Blaker | 351/161 |
| 4,636,211 | 1/1987 | Nielsen et al. | 623/6 |
| 4,637,697 | 1/1987 | Freeman | 351/161 |
| 4,641,934 | 2/1987 | Freeman | 351/159 |
| 4,693,572 | 9/1987 | Tsuetaki et al. | 351/161 |
| 4,704,016 | 11/1987 | de Carle | 351/161 |
| 4,720,286 | 1/1988 | Bailey et al. | 623/6 |
| 4,752,123 | 6/1988 | Blaker | 351/161 |
| 4,759,762 | 7/1988 | Grendahl | 351/161 |
| 4,813,955 | 3/1989 | Achatz et al. | 623/6 |
| 4,890,912 | 1/1990 | Visser | 351/161 |
| 4,890,913 | 1/1990 | DeCarle | 351/161 |
| 4,898,461 | 2/1990 | Portney | 351/161 |
| 5,166,711 | 11/1992 | Portney | 351/161 |
| 5,166,712 | 11/1992 | Portney | 351/161 |
| 5,225,858 | 7/1993 | Portney | 351/161 |
| 5,270,744 | 12/1993 | Portney | 351/161 |

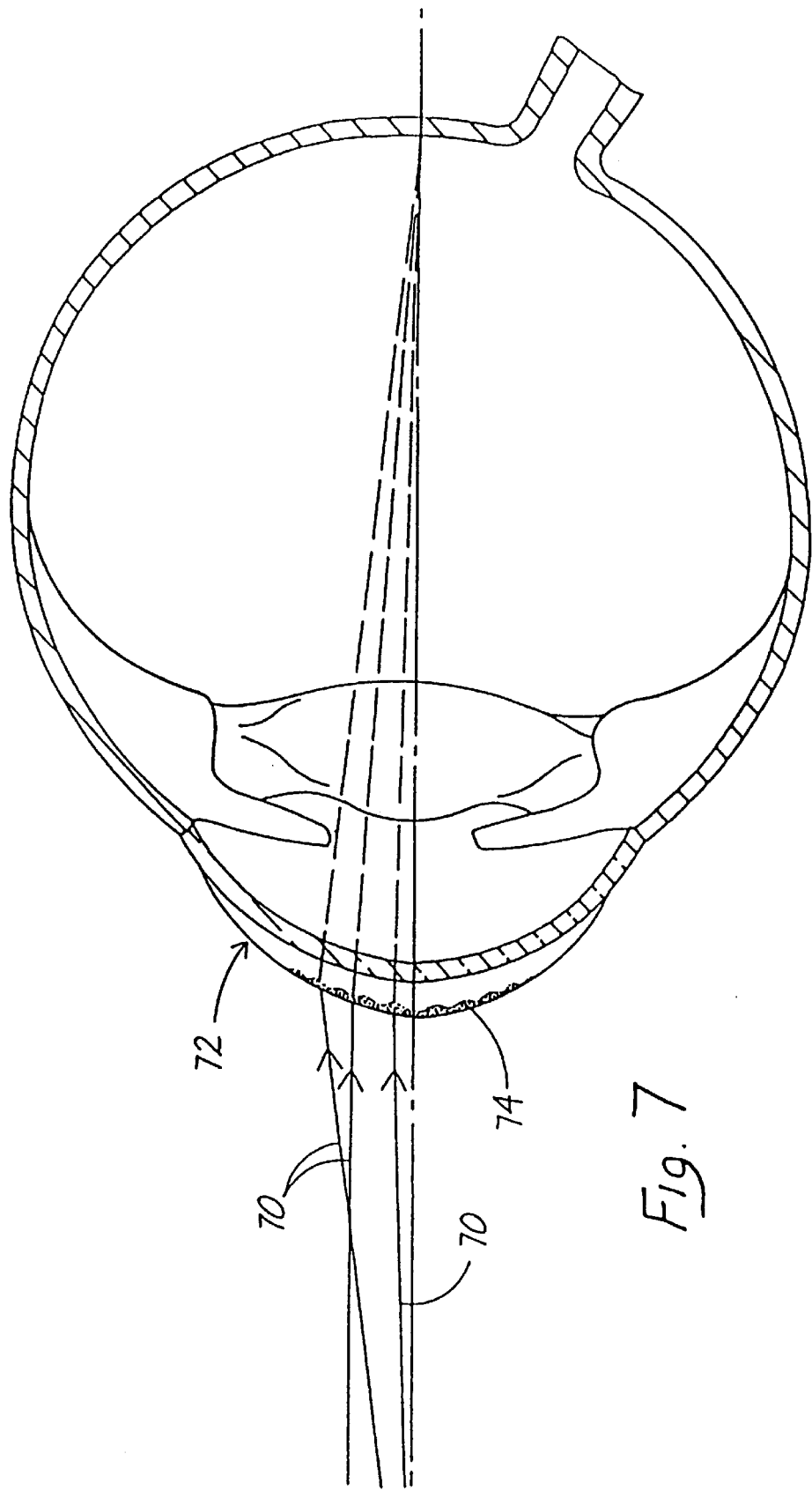

MULTIFOCAL OPHTHALMIC LENS

This application is a division of application Ser. No. 08/592,164 filed Jan. 26, 1996 now U.S. Pat. No. 5,657,108 which is a division of application Ser. No. 08/122,822 filed Sep. 16, 1993 now U.S. Pat. No. 5,521,656 which is a division of application Ser. No. 07/935,586 filed Aug. 26, 1992 now U.S. Pat. No. 5,270,744 which is a division of application Ser. No. 07/465,477 filed Jan. 16, 1990 now U.S. Pat. No. 5,166,712 which is a division of application Ser. No. 07/366,319 filed Jun. 14, 1989 now U.S. Pat. No. 4,898,461 which is a continuation of application Ser. No. 07/056,050 filed Jun. 1, 1987 now abandoned.

BACKGROUND OF THE INVENTION

This invention relates to ophthalmic lenses, e.g., intraocular lenses (IOLs), contact lenses, and corneal implant and onlay lenses; and it concerns the problem of providing ophthalmic lenses which successfully handle bifocal, and other multifocal, corrections.

Where spectacles, or eyeglasses, are used, the movement of the eyes relative to the lenses selects the different focal powers for near and far vision. Where ophthalmic lenses are used, other means must be provided for such selection. At least three types of lens designs, primarily for contact lenses, have been suggested as possible means of satisfying this need. In each of these types of contact lens designs, problems have been encountered, primarily due (a) to the need for centering of the lens on the eye, and (b) to the effects of normal changes in the size of the eye's pupil.

One form of multifocal ophthalmic lens design is illustrated by U.S. Pat. No. 4,593,981, which discloses a bifocal contact lens designed to correct for near vision in the center portion of the lens and for far vision in the peripheral portion of the lens. With this type of lens, centering on the eye is essential for satisfactory performance; and correct size of the optical zones is also important. If either of these requirements is not met, a lens of this type can produce diplopia or fringing.

Another form of multifocal ophthalmic lens design is illustrated in U.S. Pat. No. 4,580,882, which discloses a multifocal contact lens having optical power which continuously varies from minimum at the optical center point to maximum at the periphery of the optical zone. Usually this progressive (aspheric, variable focus) type of lens is constructed with a centrally placed small zone of constant curvature from which aspheric curves are grown towards the periphery in all meridians. The central area serves as the power for the distant correction, while the peripheral curves provide a varying amount of additive plus power for the near point. The curves may be placed on the front surface in which case they increase in convexity, or on the back surface in which case they decrease in concavity (flatten). If the surface of progressive curvature is placed on the front of the lens, the tear layer interferes with the lens performance. If the progressive curvature is placed on the back surface of the lens, this will affect the fitting characteristics of a contact lens. In both cases the image is "undercorrected", which is more natural for human vision. This "progressive" power lens has the advantage that flare or diplopia does not occur if the lens is slightly off-center. However, pupil size affects vision with this lens, as it does with the lens discussed in the preceding paragraph.

A third form of multifocal ophthalmic lens design is illustrated in U.S. Pat. Nos. 4,549,794 and 4,573,775 which disclose bifocal contact lenses of the segmented type, i.e., lenses in which a segment having different refractive characteristics is embedded at a selected position in the lens body. The segments are positioned along the vertical axes. Lenses of this type do not have symmetry around their centers; and they require some form of ballast to assure maintaining the desired orientation. Deviation from proper orientation affects the image quality.

One attempt to solve the centralization and orientation problems in a bifocal lens is represented by U.S. Pat. No. 4,162,122, which discloses a zonal bifocal contact lens in which annular concentric zones alternate between the near and far vision powers. This is accomplished by providing an anterior lens surface having characteristics similar to a Fresnel lens, except that sharp zonal edges are avoided. This structure has disadvantages due to the multiple diffraction caused by the abrupt curvature change of the lens surface from one zone to another; and also due to uncertainty as to the tear layer distribution on the anterior surface of the contact lens.

Designs similar to those described above are proposed also for intraocular lenses: e.g., U.S. Pat. No. 4,636,211 and European Patent 0-140-063. Both of them describe several zones of different curvatures for far and near vision. Continuity of the surface curvature is also important for an intraocular lens because it has an effective optical zone of only 3 mm diameter for daytime vision. Disruption of this relatively small optical zone can reduce the image performance. Besides, such lenses suffer from all of the problems described for contact lenses.

In general, multifocal ophthalmic lenses previously developed have tended to provide unstable optical systems because of random changes in lens position relative to the pupil of the eye, and also because of changes in the pupil size which significantly affect the imaging performance.

SUMMARY OF THE INVENTION

The present invention provides an improved multifocal ophthalmic lens by combining (a) a series of alternating power zones with (b) a continuously varying power within each zone as well as in transition from one zone to another. In other words, a plurality of concentric zones (at least two) are provided in which the variation from far to near vision correction is continuous, i.e., from near correction focal power to far correction focal power, then back to near, and again back to far, or vice versa. This change is continuous (progressive), without any abrupt correction changes, or "edges". The construction may also be such that the radial width of the zone for far-to-near transition is larger than the radial width of the zone for near-to-far transition, in order to provide "undercorrected" performance of the lens overall.

Two versions of the invention are disclosed. In the first version continuous, alternating power variation is accomplished by a continuously changing curvature of the lens posterior surface, thereby altering the angle of impact of light rays on the eye.

In the second version continuous, alternating power variation is accomplished by creating non-homogeneous surface characteristics having refractive material indexes which continuously vary in tile lens radial direction (out from the optical axis). This technique has a similar effect to the aspherizing of the surface by utilizing continuous curvature variation as described above. Such surface refractive variations may be provided either on the convex anterior or on the concave posterior surface of the lens. This variation in the refractive index may be accomplished by ion-implantation techniques. This approach is particularly suitable for a corneal implant (corneal inlay) or a corneal onlay (the former is implanted inside the cornea, and the latter is placed between the corneal epithelium layer and the anterior surface of the cornea).

BRIEF DESCRIPTION OF THE DRAWINGS

FIG. 7 is a cross-section of a contact lens, in which the forward, or anterior, convex surface of the lens has a varying refractive index gradient of the material in the radial direction, in order to obtain the same result as the lens in FIGS. 4, 6A and 6B, but using refractive index variations instead of surface curvature variations.

DETAILED DESCRIPTION OF SPECIFIC EMBODIMENTS

Figure 1:
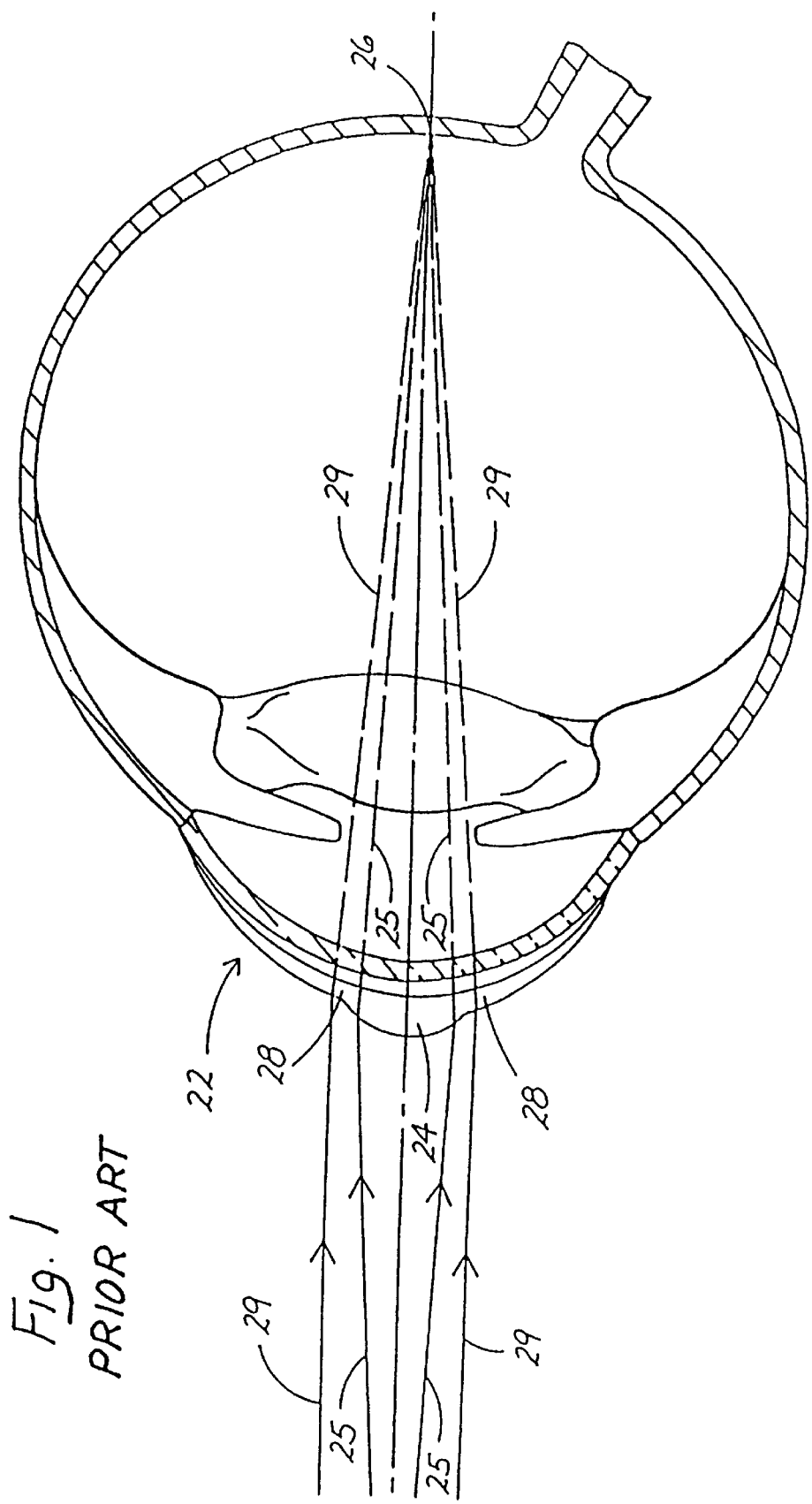
FIGS. 1–3 are sketches illustrating the three general prior art approaches discussed above.

FIG. 1 illustrates a prior art effort to solve the problem of forming bifocal contact lenses. A contact lens 22, shown in cross-section, has a central portion 24 designed to focus light from near objects on the retina 26, as shown by the inner lines 25 representing light rays. Contact lens 22 has a peripheral portion 28, which is designed to focus light from far objects on the retina 26, as shown by the outer lines 29 representing light rays.

The bifocal lens of FIG. 1 can only focus objects located at specific distances (far and near) and separated. Also, it clearly is subject to problems due to any displacement from centrality of the lens on the eye, and due to changes in the size of the eye's pupil.

Figure 2:
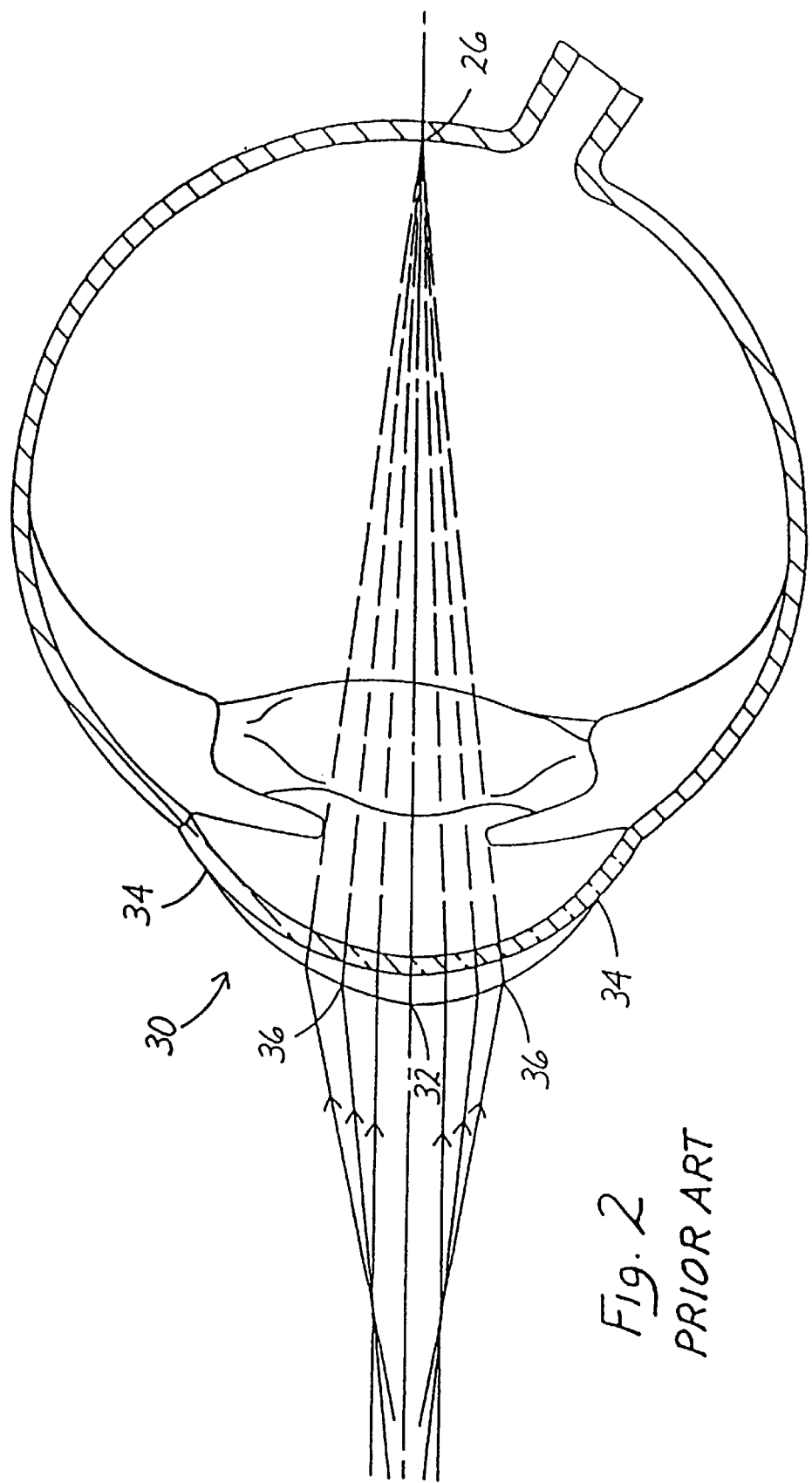

FIG. 2 illustrates another prior art effort to solve the problem of forming varying focus contact lenses. A lens 30 is shown in cross-section, having its center at 32 and its periphery at 34. Because of its continuously changing curvature from its center to its periphery, it provides a continuous change of focusing power from viewing far objects at the center to viewing near objects at the periphery, within a range of, say, two diopters, as illustrated by the lines 36 representing retina-focused light rays. The central ray at 32 is from the farthest object viewed, and the focused rays 36 are progressively from nearer objects, as their contact points on lens 30 move closer to its periphery.

This continuous variation in lens power has advantages over the arrangement of FIG. 1, from the standpoint of being more easily accepted by the retina and the brain. It also is less susceptible to centering problems, i.e., flare or double image has not been reported for this type of lens if it is slightly decentered. However it is negatively affected by variations in pupil size and by large decentration; and also this lens type tends to create fitting problems between the posterior surface of the lens and the cornea.

Figure 3:
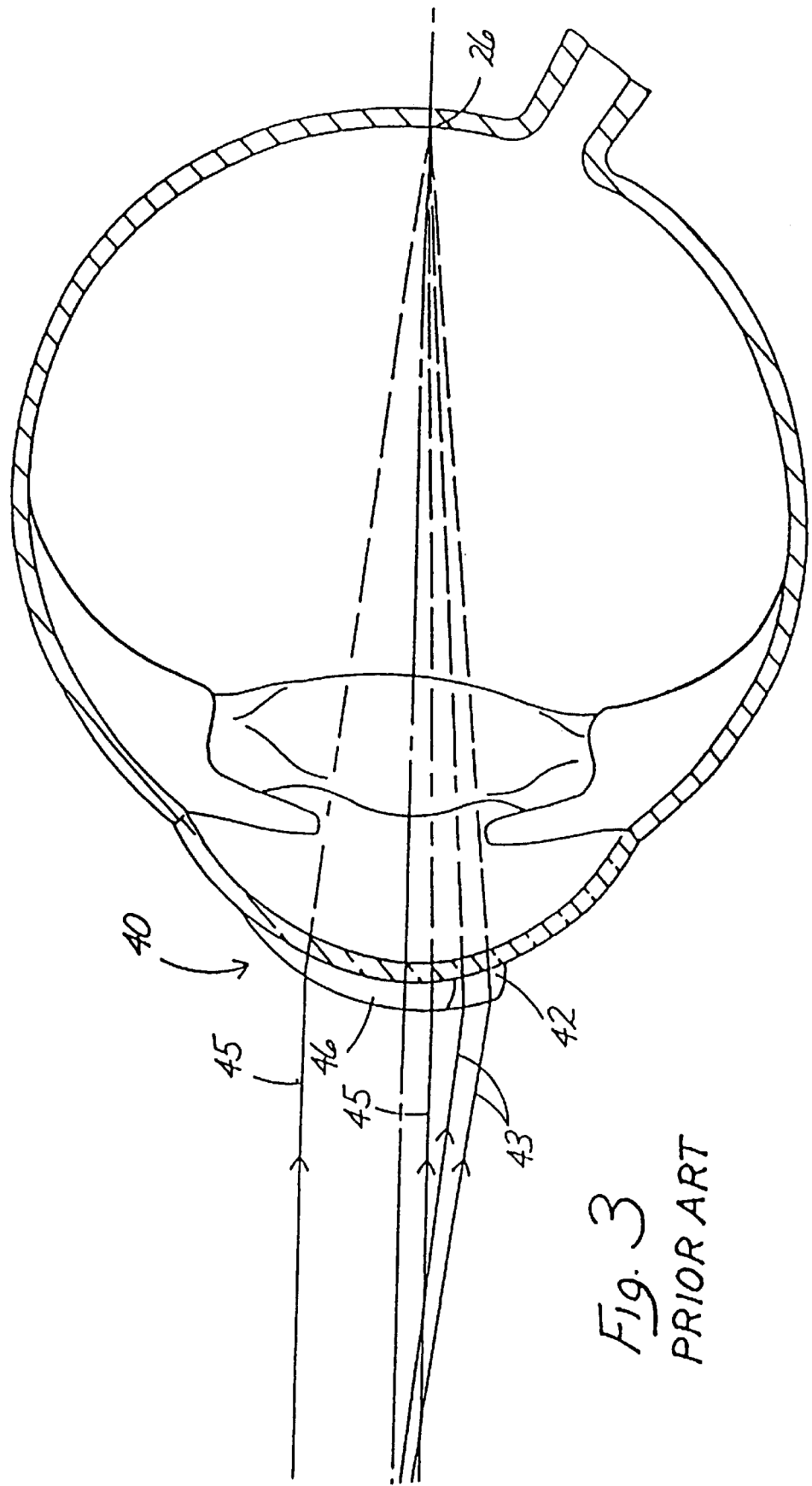

FIG. 3 illustrates a third prior art approach, which is conceptually similar to bifocal spectacles. A contact lens 40 includes an embedded segment 42 formed of material having a different refractive index from the remainder of the lens. The segment 42 is used to provide near vision correction, as shown by rays 43. The remaining rays 45, which come from farther objects, are focused at the retina because of the gradual change in thickness of the body 46 of the lens.

The lens of FIG. 3 does not have central symmetry, and requires the use of ballast to maintain the desired orientation. Deviation from proper orientation affects the image quality.

Figure 4:
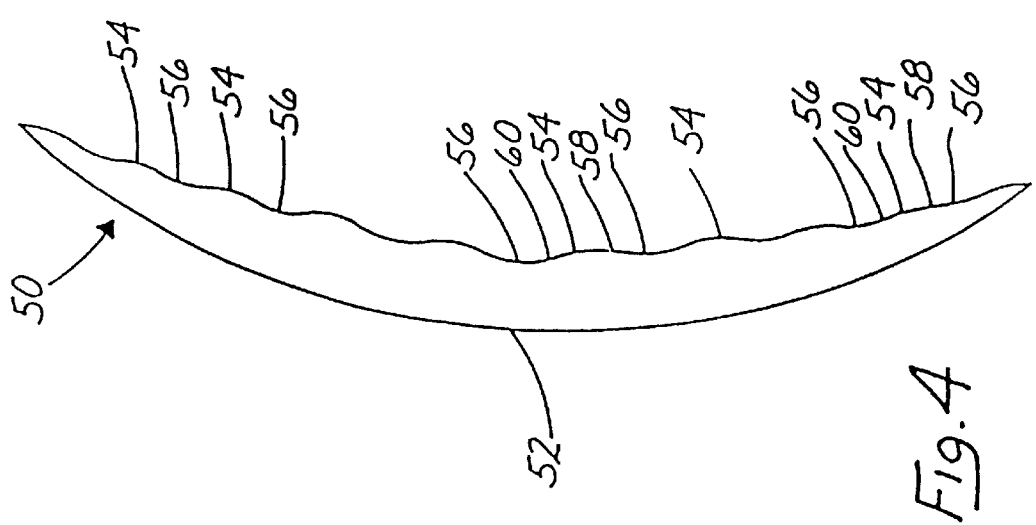
FIG. 4 is an enlarged cross-section of a contact lens, having a multi-zone, continuously-varying posterior surface. The exaggerated dimensions of the varying lens surface illustrate the concepts of the present invention.

In order to minimize the problems due to the need for centering, due to pupil size variation, and due to fitting requirements (progressive type), the present invention, as shown in FIG. 4, uses several zones, each of which includes a progressive power change from near correction to far correction. In other words, in a three-zone contact lens, the progressive variation of the FIG. 2 lens would be repeated six times, three times as a variation from lower to higher power, and three times as a variation from higher to lower power. The lens is constructed with a small centrally placed zone of constant curvature to form the power for middle correction. From it the curvature changes to far correction, then to near correction, passing through the middle correction. This alternation is continued to form several zones. It is considered desirable, but not necessary, to have slower variation from far-to-near correction and faster variation from near-to-far correction, in order to form in general some "undercorrection", as found in most visual instruments.

FIG. 4 shows a contact lens 50, the outer convex surface 52 of which has a smooth arcuate shape, and the inner surface of which has an undulating surface, as seen in very exaggerated dimensions in the figure. The inner surface of a contact lens is much preferred as the variable power, or undulating, surface, because the space between the lens and the eye will be filled with tears having a predetermined varying depth. This predetermined depth of tears permits the refractive effect of the tears to be compensated for in the design of the lens. If the undulating surface were formed on the exterior surface 52 of the lens, the uncertainty of the tear layer distribution would tend to prevent optimal imaging.

Figure 5:
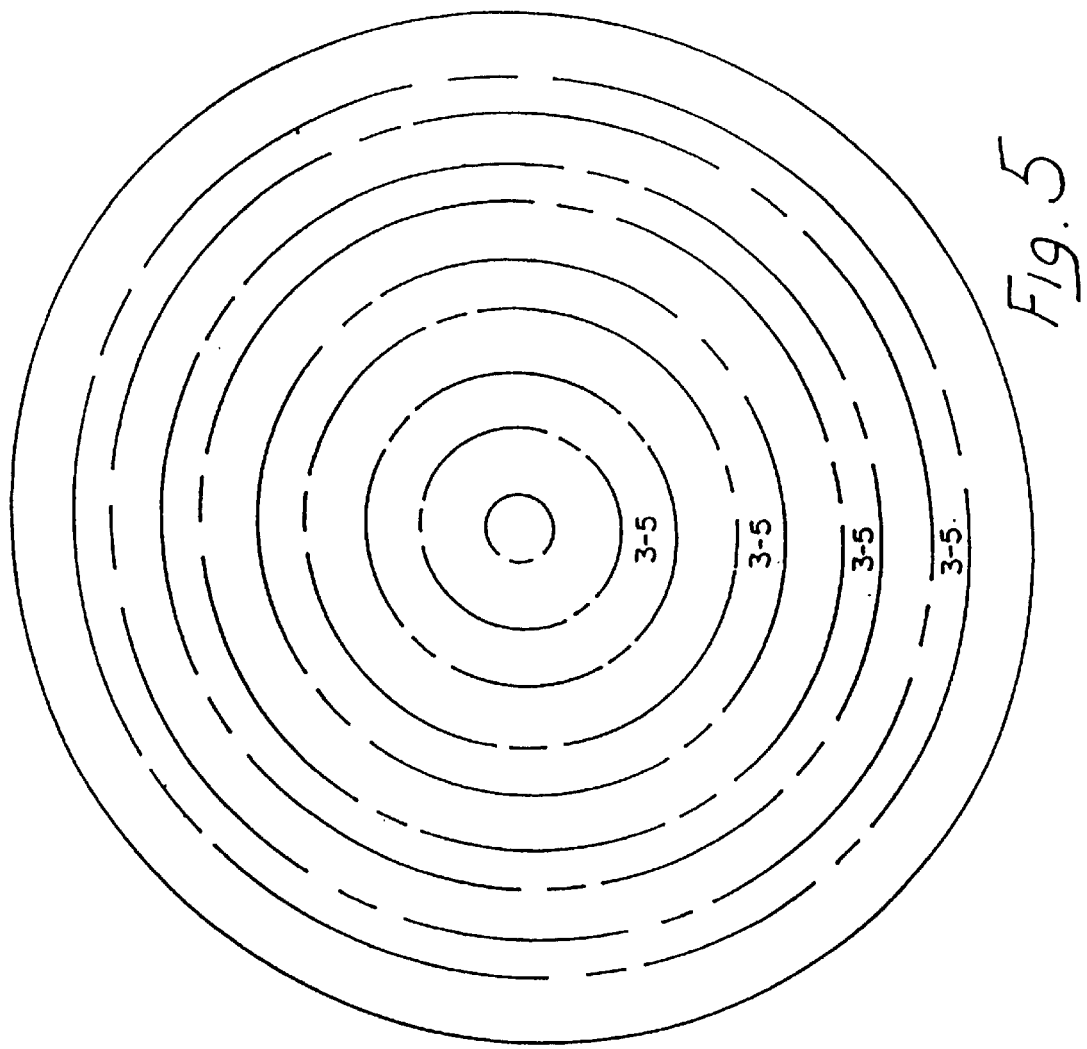
FIG. 5 is a front view of the posterior of the lens of FIG. 4, illustrating the concentric arrangement of the peaks and valleys of the lens surface.

The view from the right side (posterior) of the proposed lens is shown in FIG. 5. The zones shown by dashed lines in reality have a continuous curvature, e.g., the numbers inside each zone represent the range of diopters.

The lens has a constraint placed on its posterior surface determined by the fitting characteristics for a given cornea. Usually the back surface of a contact lens (base curve) is from 0.5 to 1.0 diopter steeper than the corneal shape, which translates to approximately 0.1 mm to 0.2 mm distance between the inner, or posterior, surface of the contact lens and the front surface of the cornea. This is usually the case in single focus contact lenses. The undulations in the posterior surface of lens 50 in FIG. 4 represent a distance difference, or maximum depth, of less than 20 microns between the peaks 54 and valleys 56 (as they would appear if FIG. 4 were rotated 90° counterclockwise). The zones are placed within a dimensional range (diameter) of the lens of about 5 mm; and within this range the peak-to-valley differences are always much smaller than the available gap between lens and cornea. This significantly simplifies the fitting requirements, as the regular single vision lens can be fitted first and then replaced with the multifocal lens of similar base curve configuration.

The peaks 54 and valleys 56, which occur at points tangent to circles having their centers at the center of the outer curvature 52 of the lens, represent the intermediate focal distances, or optical correction power, of the continuously varying correction values of the lens 50. The higher and lower corrective powers in each zone of the four annular concentric zones shown in FIG. 4, occur as the undulating curve progresses from one peak 54 to the adjacent valley 56, and then back to the next peak 54. Except for the small centrally placed zone of constant curvature which provides power for middle correction, a zone is considered to include a complete cycle, i.e., from the intermediate power through the high power, then back through the intermediate power to the low power, and finally back to the intermediate power.

Figure 6A:
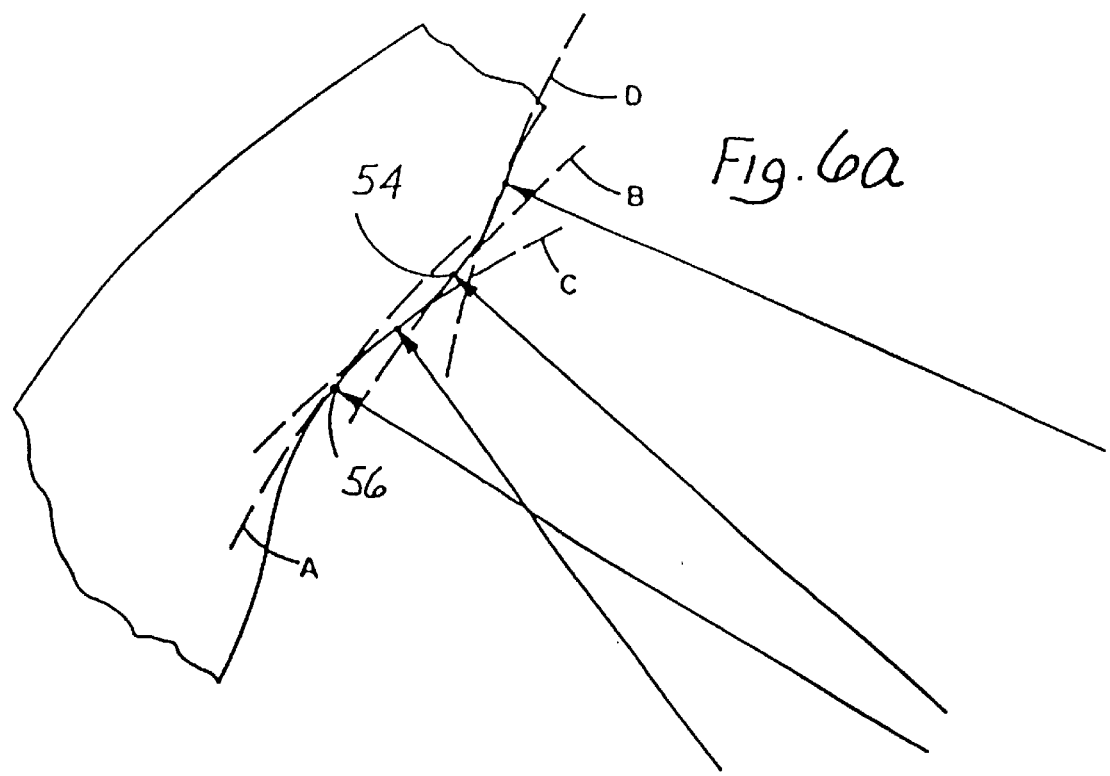
FIGS. 6A and 6B are further enlarged closeups of a small portion of the posterior lens surface of FIG. 4, used to explain the focusing effects of light rays from near and far locations.
Figure 6B:
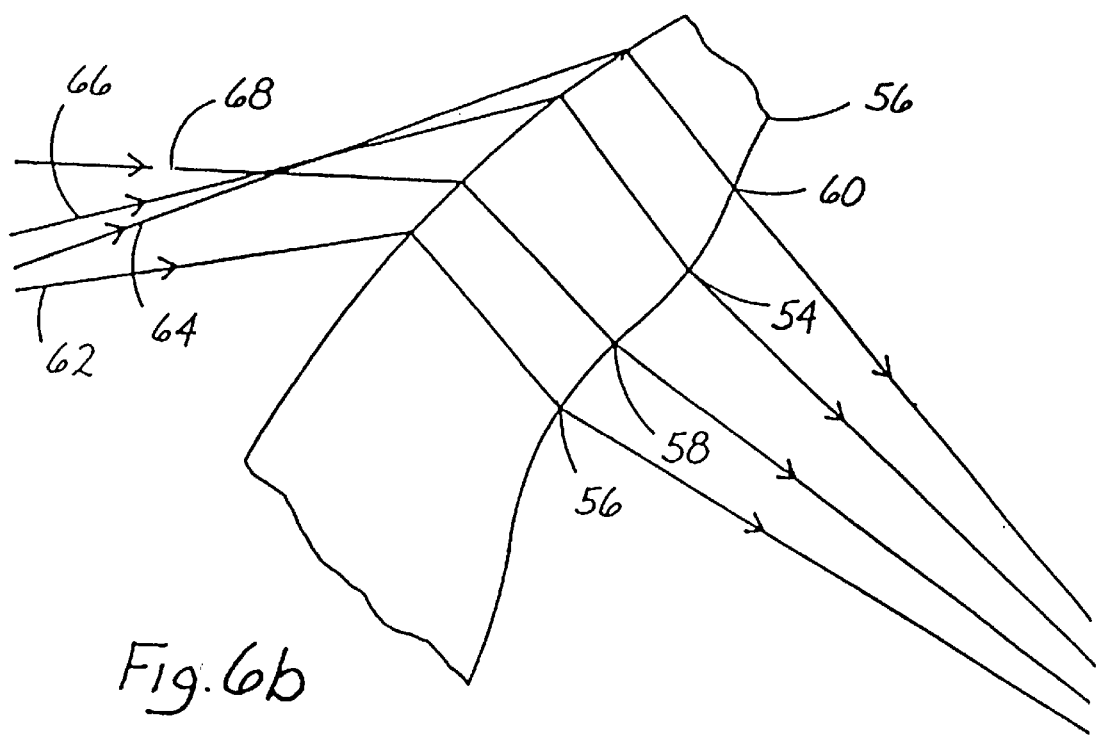

This is illustrated in the highly enlarged FIGS. 6A and 6B. As seen in FIG. 6B, a first ray 62, from an object at an intermediate distance, passes through a valley 56 in the posterior lens surface. A second ray 68, from an object at a far position (lower power correction), passes through a portion 58 of the undulating curve formed as that curve progresses toward the adjacent peak 54 in the posterior lens surface. A third ray 66, from an object at an intermediate distance, passes through the peak 54. A fourth ray 64, from an object at a near position (higher power correction), passes through a portion 60 of the undulating curve formed as that curve progresses toward the next valley 56 in the posterior lens surface. All of the rays, 62, 64, 66 and 68, are focused at the retina, as shown.

FIG. 6A illustrates the principles used in formation of the undulating curve, by considering the curve as comprising progressive focal powers corresponding to individual lenses having curvatures as illustrated by the dashed lines A, B, C and D. The arcuate line A is tangent to the valley 56. The arcuate line B is tangent to the peak 54. The arcuate line C is tangent to the undulating curve at a point midway between the valley 56 and the peak 54. And the arcuate line D is tangent to the undulating curve at a point midway, between the peak 54 and the next valley. For full progressivity, each point on the undulating curve has a different radial center from the centers of the adjacent points.

The undulating surface of the lens is preferably formed by a computer-controlled machining apparatus. The computer program of this computer numerically controlled (CNC) machine generates a large number of closely spaced points (coordinates), which represent the multifocal surface for the given design requirements (curvature, range of accommodation, number of zones, etc). The computer of the CNC machine then forms a linear approximation between these points to generate a surface with good approximation to the ideal surface contour. A sample of the points is provided by the following table. In the fabrication of a three zone contact lens, with the three zones being identified by the code numbers "13M3", "23M3", and "33M3", respectively, an exemplary set of coordinates is set forth in the table. The first column of figures represents the radius of the lens aperture (distance from the lens center). The third column represents the surface coordinates along the optical axis. And the second column represents the deviation of the above surface from the spherical surface of the mid-range power.

| 13M3 | | |
| --- | --- | --- |
| .417 | −.0001 | .012 |
| .589 | −.0006 | .0236 |
| .722 | −.0013 | .035 |
| .833 | −.002 | .0465 |
| .932 | −.0023 | .0584 |
| 1.021 | −.0024 | .0705 |
| 1.102 | −.0022 | .0829 |
| 1.179 | −.0018 | .0956 |
| 1.25 | −.001 | .1086 |
| 1.318 | −.0004 | .1215 |
| 1.382 | 0.00 | .1343 |
| 1.443 | .0001 | .1457 |
| 23M3 | | |
| 1.443 | .0001 | .1467 |
| 1.616 | −.0003 | .1839 |
| 1.687 | −.001 | .2001 |
| 1.742 | −.0018 | .2127 |
| 1.789 | −.0025 | .2238 |
| 1.829 | −.0029 | .234 |
| 1.866 | −.003 | .2437 |
| 1.9 | −.0029 | .253 |
| 1.932 | −.0026 | .262 |
| 1.961 | −.0021 | .2709 |
| 1.989 | −.0017 | .2793 |
| 2.016 | −.0015 | .2872 |
| 2.041 | −.0015 | .2948 |
| 33M3 | | |
| 2.041 | −.0015 | .2948 |
| 2.174 | −.0021 | .3346 |
| 2.229 | −.0029 | .3517 |
| 2.271 | −.0038 | .3646 |
| 2.306 | −.0046 | .3758 |
| 2.337 | −.005 | .3861 |
| 2.366 | −.0051 | .3957 |
| 2.392 | −.005 | .4049 |
| 2.416 | −.0048 | .4138 |
| 2.439 | −.0043 | .4224 |
| 2.46 | −.004 | .4306 |
| 2.48 | −.0038 | .4383 |
| 2.5 | −.0038 | .4455 |

It is understood that alternate methods of manufacture are available, such as laser ablation or molding.

FIG. 7 illustrates another embodiment of the present invention. In this figure the optical gradient is produced by variations in the refractive index of the material reached by the rays 70. The refractive variations are preferably provided on the anterior convex surface of the lens 72. This is preferred because the probable manufacturing method will utilize ion-implantation techniques to produce density variations at the surface of the lens; and it is considered a safety precaution to have the ion-implanted surface on the side of the lens away from the eye.

Although FIG. 7 shows depth variations (in the shaded area 74) to illustrate the invention, in practice the refractive variations might involve density variations, rather than depth variations, or both.

In producing the lens 72 of FIG. 7, ion implantation can be used to increase the index of refraction, as the result of lattice disorder produced by non-substitutional implanted ions. For example, by implantation of fused quartz thick-film-deposited on the lens substrate with ions of nitrogen or other elements, a layer of increased index of refraction is produced. The index of refraction is directly proportional to the ion concentration per $cm^3$. The depth of penetration of the implanted ions depends on their mass and energy. Knowing the penetration characteristics and the implanted ion dose per $cm^2$, which can be determined very accurately by measuring beam current density of the system and implant time, one can calculate the profile of implanted ion concentration at varying depths. As with any particles with charges, the electromagnetic lenses and beam scanner can be used to form practically any variation of ion concentration at the substrate, and particularly to form progressive zonal lens having the optical characteristics of FIGS. 6A and 6B. Similar results can be achieved by using masks of varied density. The vision corrective effect would correspond to that produced by the posterior surface undulations in the lens of FIG. 4.

Figure 8A:
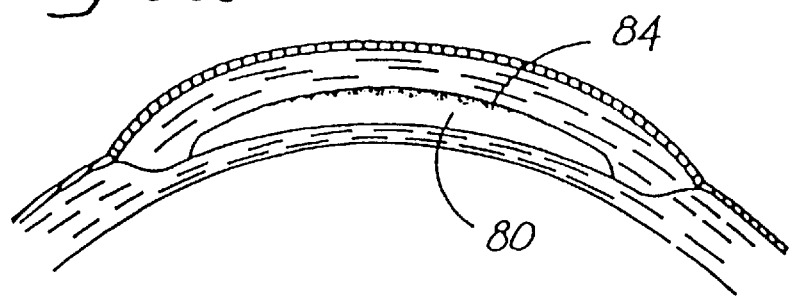
FIGS. 8A, 8B and 8C are cross-sections, respectively, of a corneal implant lens, a corneal onlay lens and an intraocular lens, anyone of which may have its anterior or posterior surface formed similarly to the posterior contact lens surface shown in FIG. 4.
Figure 8B:
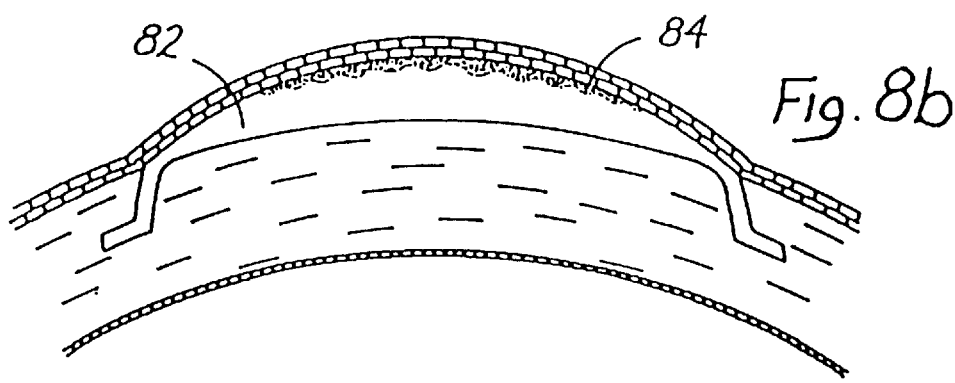
Figure 8C:
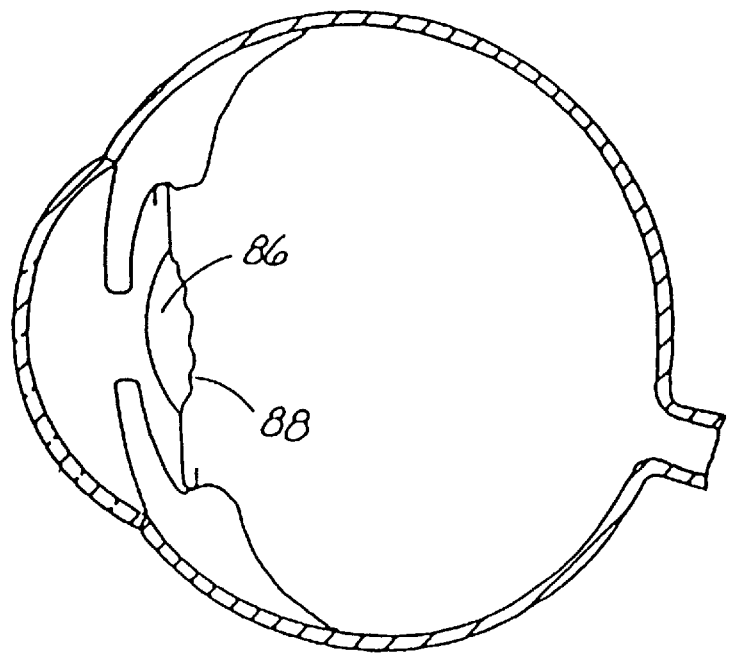

FIGS. 8A, 8B and 8C show, respectively, a corneal inlay lens, a corneal onlay lens, and an intraocular lens, each incorporating the concepts of the present invention. In the corneal inlay lens 80 of FIG. 8A, and in the corneal onlay lens 82 of FIG. 8B, the illustrated progressive zonal variations are accomplished with the variable refractive index of lens material 84, as described in conjunction with FIG. 7.

In the intraocular lens 86 of FIG. 8C, the posterior surface 88 is shown as an undulating surface having progressive zonal variations comparable to those in FIG. 4.

Any of the three lens implants of FIGS. 8A, 8B or 8C could use either the surface variations or the refractive index variations, and also could use either the anterior or posterior surface as the multifocal surface.

The implanted lenses of FIGS. 8A, 8B and 8C are subject to the same problems as are the contact lenses, e.g., pupil size variations and decentration problems. The pupil size problems are essentially the same. The decentration problems are less pronounced with implanted lenses, but are nevertheless significant because operational procedures do not insure centration, and, in the case of intraocular lenses, postoperative movement can be quite noticeable.

From the foregoing description, it will be apparent that the apparatus and methods disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. A method of vision correction comprising shaping first, second and third regions of a surface to provide the first region with a first vision correction power, the second region with a second vision correction power which is different from the first vision correction power to enhance vision at first and second different distances, respectively, and the third region between said first and second regions to provide progressive vision correction powers which include progressive vision correction powers which are between the first and second vision correction powers.

2. A method of vision correction as defined in claim 1 wherein the step of shaping is carried out to provide the first region with a near vision correction power and the second region with a far vision correction power.

3. A method of vision correction as defined in claim 1 wherein the step of shaping includes shaping a fourth region of the surface to provide progressive vision correction powers which include progressive vision correction powers which are between the first and second vision correction powers, said second region being between the third region and the fourth region.

4. A method of vision correction comprising:
shaping first and second annular regions of a surface to provide the first region with a first vision correction power and the second region with a second vision correction power which is different from the first vision correction power to enhance vision at first and second different distances, respectively; and shaping a third annular region of the surface between said first and second regions to provide progressive vision correction powers which include progressive vision correction powers which are between the first and second vision correction powers, said second annular region circumscribing the first annular region.

5. A method of vision correction as defined in claim 4 including shaping a fourth annular region of the surface to provide progressive vision correction powers which include progressive vision correction powers which are between the first and second vision correction powers, said fourth annular region circumscribing the second annular region.

6. A method of vision correction as defined in claim 4 including shaping a central region of the surface to provide a vision correction power intermediate the first and second vision correction powers, said first annular region circumscribing the central region.

7. A multifocal surface with a first region having a configuration which provides a first vision correction power, a second region having a configuration which provides a second vision correction power which is different from the first vision correction power to enhance vision at first and second different distances, respectively, and a third region between the first and second regions having a configuration which provides progressive vision correction powers which include progressive vision correction powers which are between the first and second vision correction powers.

8. A multifocal surface as defined in claim 7 wherein the first and second distances are near and far, respectively.

9. A multifocal surface as defined in claim 7 wherein the first, second and third regions are annular and the second region circumscribes the first region.

10. A multifocal surface as defined in claim 7 which has a fourth region with a surface configuration to provide progressive vision correction powers which include progressive vision correction powers which are between the first and second vision correction powers, said second region being between the third region and the fourth region.

11. A multifocal surface as defined in claim 10 wherein each of said first, second, third and fourth regions of the surface is annular with the third region circumscribing the first region, the second region circumscribing the third region and the fourth region circumscribing the second region.

12. A multifocal surface as defined in claim 11 wherein the progressive vision correction powers include progressive vision correction powers which increase in a radial direction across one of the third and fourth regions and decrease in said radial direction across the other of the third and fourth regions.

13. A multifocal surface as defined in claim 12 wherein the anterior surface has a central region circumscribed by the first region which provides a vision correction power intermediate the first and second vision correction powers.

14. A multifocal surface having progressive vision correction powers in first and second at least partially annular regions, said second region at least partially circumscribing the first region, the progressive vision correction powers of one of said first and second regions including progressive vision correction powers which increase in a radial outward direction and the progressive vision correction powers of the other of said first and second regions including progressive vision correction powers which decrease in a radial outward direction.

15. A multifocal surface as defined in claim 14 wherein said first region is substantially completely annular.

16. A multifocal surface as defined in claim 15 wherein said second region substantially completely circumscribes the first region.

17. A multifocal surface as defined in claim 14 wherein the progressive vision correction power of each of the first and second regions varies between near and far vision correction powers.

18. A multifocal surface having progressive vision correction powers in first, second, third and fourth at least partially annular regions, said second, third and fourth regions at least partially circumscribing the first, second and third regions, respectively, the first and third regions constituting a first set of regions and the second and fourth regions constituting a second set of regions, the progressive vision correction powers of said first set of regions including progressive vision correction powers which increase in a radial outward direction and the progressive vision correction powers of said second set of regions including progressive vision correction powers which decrease in a radial outward direction.

19. A multifocal surface having first and second zones with the second zone circumscribing the first zone, said first zone including in radial outwardly extending order a first vision correction power, progressive vision correction powers, a second vision correction power and progressive vision correction powers, said first and second vision correction powers being different and said progressive vision correction powers including progressive vision correction powers between the first and second vision correction powers, said second zone including in radial outwardly extending order a third vision correction power, progressive vision correction powers, a fourth vision correction power and progressive vision correction powers, said third and fourth vision correction powers being different and the progressive vision correction powers of the second zone including vision correction powers between the third and fourth vision correction powers, said surface having a central zone which includes a power intermediate the first and second vision correction powers, said zones being concentric with the first zone circumscribing the central zone.

\* \* \* \* \*